United States Patent [19]

Regna

[11] Patent Number: 4,796,630
[45] Date of Patent: Jan. 10, 1989

[54] CARDIAC PACEMAKER WITH COMBINED DEFIBRILLATION AND ELECTROSURGERY PROTECTION

[75] Inventor: Richard C. Regna, Miami, Fla.

[73] Assignee: Telectronics N.V., Netherlands Antilles

[21] Appl. No.: 28,753

[22] Filed: Mar. 23, 1987

[51] Int. Cl.$^4$ .................. A61N 1/00; H05G 00/00
[52] U.S. Cl. ................ 128/419 D; 128/419 P; 128/908
[58] Field of Search .......... 128/419 D, 419 R, 419 P, 128/419 PT, 420 R, 303 B, 901, 908

[56] References Cited

U.S. PATENT DOCUMENTS

| | | | |
|---|---|---|---|
| 3,518,986 | 11/1967 | Woods et al. | 128/908 |
| 3,968,802 | 7/1976 | Ballis | 128/908 |
| 4,147,162 | 4/1979 | Gatzke | 128/419 D |
| 4,153,049 | 5/1979 | Gatzke et al. | 128/419 D |
| 4,165,749 | 8/1979 | Cansell | 128/419 D |
| 4,168,711 | 9/1979 | Cannon, III et al. | 128/419 D |
| 4,202,340 | 5/1980 | Langer et al. | 128/419 D |
| 4,263,919 | 4/1981 | Levin | 128/901 |
| 4,301,801 | 11/1981 | Schneiderman | 128/908 |
| 4,440,172 | 4/1984 | Langer | 128/419 D |
| 4,595,009 | 6/1986 | Leinders | 128/419 D |

Primary Examiner—Francis Jaworski
Assistant Examiner—George Manuel
Attorney, Agent, or Firm—Pigott & Gerstman, Ltd.

[57] ABSTRACT

A cardiac pacemaker is provided which has combined defibrillation and electrosurgery protection. The pacemaker includes an implantable housing with a pacing circuit located within the housing and means for attaching a lead to the housing. A protection circuit is located between the pacing circuit and the attaching means. The protection circuit comprises a zener diode and a capacitor connected across the zener diode. The capacitor has a value to provide a relatively low impedance with respect to electrosurgery frequencies and a relatively high impedance with respect to cardiac myopotential frequencies.

10 Claims, 1 Drawing Sheet

CARDIAC PACEMAKER WITH COMBINED DEFIBRILLATION AND ELECTROSURGERY PROTECTION

FIELD OF THE INVENTION

The present invention concerns a novel cardiac pacemaker having combined defibrillation and electrosurgery protection.

BACKGROUND OF THE INVENTION

In electrosurgery, an electric scalpel is used to provide for cauterization as it cuts. The voltages that are generated by the electric scalpel may result in fibrillation if the pacer loop causes demodulation of the waveform. German standard DIN VDE 0750 Part 9 provides a test to determine if the pacer has suitable electrosurgery protection, i.e., a determination is made as to whether the pacer loop caused demodulation. The German standard requires that with a 500 kilohertz waveform that is 100 percent modulated at 50 hertz with 10 volts (20 volts peak to peak), applied to a series detection network (an ES demodulation detector) in the pacing loop, there would be no demodulation of the 50 hertz waveform.

In the prior art, back to back zener diodes have been used as the electrosurgery protection circuit. In one prior art embodiment the zener diodes that are used have a 9.1 voltage drop in the reverse direction and a 1 volt breakdown voltage in the forward direction. Therefore, the back to back diodes effectively have a 10.1 volt breakdown voltage in both directions. That breakdown voltage just exceeds the 10 volts of the German standard test waveform. Thus there will be no conduction in the diodes resulting in no demodulation.

However, while the back to back diodes are satisfactory for preventing the demodulation under the German Standard test, they are not satisfactory for protecting against defibrillation potentials. The defibrillation potentials are as high as 400 joules and would be applied typically by paramedics or physicians in the event that the patient went into fibrillation. Thus the back to back diodes do not protect against the defibrillation potentials because such defibrillation potentials may cause undesirable current flows within the pacer circuit and undesirable biasing of various elements of the pacer circuit. The defibrillation potential may cause a breakdown of the zener diodes resulting in 10 volts being applied across the tip and ring. The 10 volts that is applied across the tip and ring may cause current flows and improper biasing of some of the circuit elements as just discussed.

It is an object of the present invention to provide a circuit that prevents demodulation and also protects against the defibrillation voltages.

Another object of the present invention is to provide a protection circuit that is simple in construction and efficient to manufacture.

Other objects and advantages of the invention will become apparent as the description proceeds.

SUMMARY OF THE INVVENTION

In accordance with the present invention, a cardiac pacemaker is provided having combined defibrillation and electrosurgery protection. The pacemaker includes an implantable housing, a pacing circuit located within the housing and means for attaching a lead to the housing. A protection circuit is located between the pacing circuit and the attaching means. The protection circuit comprises a voltage breakdown device and a capacitor connected across the voltage breakdown device. The capacitor has a value to provide a relatively low impedance with respect to electrosurgery frequencies and a relatively high impedance with respect to cardiac myopotential frequencies.

In the illustrative embodiment, the voltage breakdown device comprises a zener diode having a sufficiently high breakdown voltage to avoid demodulation of electrosurgery signals.

In one embodiment, the attaching means is provided for attaching a lead in a bipolar configuration with a tip and a ring and the protection circuit is connected across the tip and ring. In this embodiment, the zener diode provides a relatively high breakdown voltage in only one direction across the tip and ring.

In another embodiment, the attaching means is provided for attaching a lead in a unipolar configuration with a tip and with the housing forming the other electrode. The protection circuit is connected across the tip and case in this other embodiment and the zener diode provides a relatively high breakdown voltage in only one direction across the tip and the case.

A more detailed explanation of the invention is provided in the following description and claims, and is illustrated in the accompanying drawings.

DETAILED DESCRIPTION OF THE ILLUSTRATIVE EMBODIMENT

Figure 1:
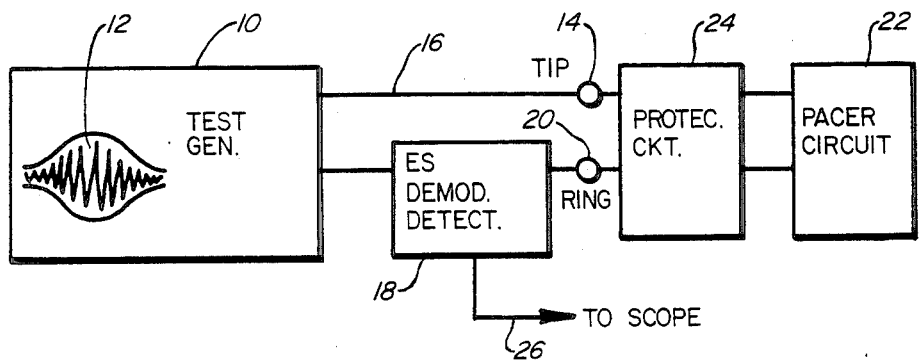
FIG. 1 is a block diagram of a test circuit for use with the present invention.

Referring to FIG. 1, a test circuit is shown therein designed to detect whether the pacer demodulates electrosurgical signals. A test generator 10 provides the source of test signals pursuant to German Standard DIN VDE 0750 Part 9. The signal comprises a 500 kilohertz waveform that is 100 percent modulated at 50 hertz having a peak to peak voltage of 20 volts. The waveform is applied to tip 14 via line 16 and through an electrosurgery demodulation detector 18 to case or ring 20.

Tip 14 and case or ring 20 are associated with pacer circuit 22 in which the electrosurgery protection circuit 24 is interposed between the pacer circuit 22 and the tip/ring. The output of electrosurgery demodulation detector 18 is connected via line 26 to an oscilliscope for viewing whether demodulation occurs when the simulated electrosurgery waveform 12 is generated.

Figure 2:
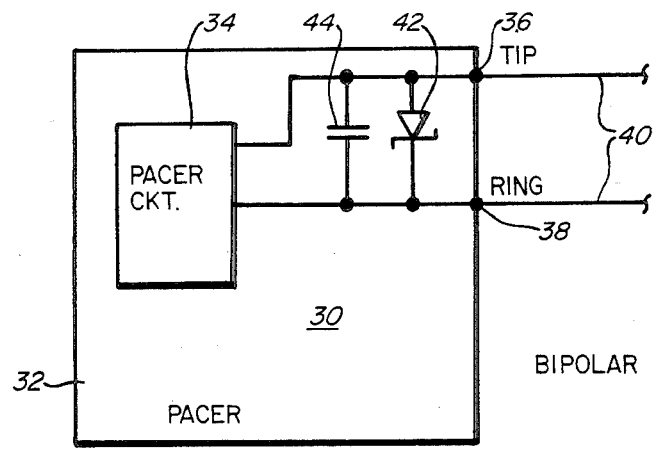
FIG. 2 is a block diagram of a bipolar embodiment of a cardiac pacemaker constructed in accordance with the principles of the present invention.

In the present invention, a cardiac pacer is provided in which a protection circuit is used which prevents the pacer from demodulating electrosurgery signals and provides improved defibrillation protection. To this end, referring to FIG. 2 a pacer 30 has a housing 32 within which is located a conventional pacer circuit 34, which may be an integrated circuit chip. Housing 32 has conventional attachment means 36 and 38 for connecting a lead 40 to the housing 32. Lead 40 in FIG. 2 comprises a tip electrode which is attached via attaching means 36 and a ring electrode which is attached via attaching means 38.

Interposed between attaching means 36, 38 and the pacer circuit 34 is a protection circuit comprising a voltage breakdown device 42 such as a zener diode and a capacitor 44 connected across the voltage breakdown device 42 if the zener diode has a sufficiently high breakdown voltage to avoid demodulation of electrosurgery signals. For example, in the illustrative embodiment it is preferred that zener diode 42 have about a 9.1 volt breakdown voltage. The capacitor 44 has a value that provides a relatively low impedance with respect to electrosurgery frequencies and a relatively high impedance with respect to cardiac myopotential frequencies. For example, electrosurgery frequencies approximate 500 kilohertz and in the illustrative embodiment, the capacitor is about 0.047 microfarad, resulting in an impedance of about 7 ohms with respect to a 500 kilohertz signal. On the other hand, myopotential frequencies may be between 20 hertz and 200 hertz and the capacitor 44 will have an extremely high impedance with respect to such frequencies.

In this manner, the impedance of capacitor 44 provides a sufficiently low impedance to act as the shunt leg of a voltage divider in conjunction with an electrosurgery tool/tissue interface, attenuating the voltage to a level which prevents zener defibrillation protection diode 42 from conducting. Thus by placing the capacitor 44 across zener diode 42, the electrosurgery voltage which appears across zener diode 42 is reduced below the zener diode's forward voltage to 0.9 volts peak to peak (0.45 volts) and therefore it will not demodulate the electrosurgery signal. This will enable zener diode 42 to provide adequate defibrillation protection and also protect the elements of the pacer circuit from transients.

Figure 3:
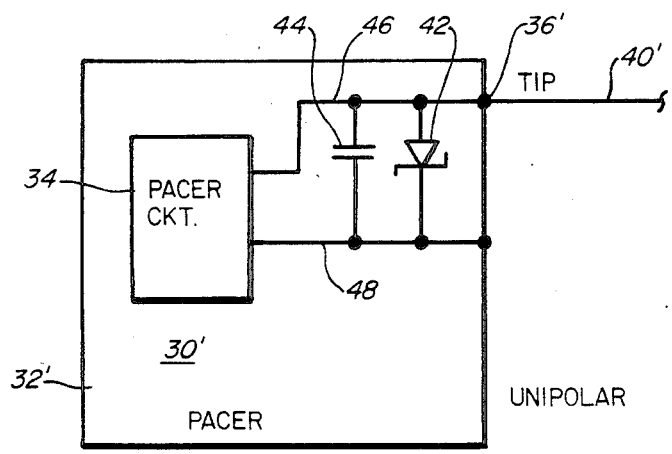
FIG. 3 is a block diagram of a unipolar pacer constructed in accordance with the principles of the present invention.

In FIG. 3, a unipolar embodiment is illustrated, including pacer 30' having a housing 32'. Housing 32' is conductive and forms an electrode. Attaching means 36' are provided for attaching the tip electrode lead 40' to the pacer circuit. Pacer circuit 34 is connected to attaching means 36' via line 46 and to conductive case 32' via line 48. Zener diode 42 and capacitor 44 are utilized as the defibrillation and electrosurgery protection circuit in the identical manner as described above with resepct to the FIG. 2 embodiment. In the FIG. 3 embodiment, as with the FIG. 2 embodiment, by connecting capacitor 44 across zener diode 42 the electrosurgery voltage that appears across the zener diode is reduced below the forward voltage across the zener diode to prevent demodulation of the electrosurgery signals. Additionally, zener diode 42 will provide adequate defibrillation protection and will protect the element of pacer circuit 34 from transients.

It is to be understood that the protection circuit may be utilized with a dual chamber pacer if desired. Although two illustrative embodiments of the invention have been shown and described, various modifications and substitutions may be made by those skilled in the art without departing from the novel spirit and scope of the present invention.

What is claimed is:

1. A cardiac pacemaker having combined defibrillation and electrosurgery protection which comprises:
   an implantable housing;
   a pacing circuit located within said housing;
   means for attaching a lead to said housing;
   a protection circuit located between the pacing circuit and said attaching means, said protection circuit comprising a voltage breakdown device and a capacitor connected across said voltage breakdown device, said capacitor having a value to provide a relatively low impedance with respect to electrosurgery frequencies and a relatively high impedance with respect to cardiac myopotential frequencies, said protection circuit having no series inductor whereby there is no tuned circuit nor is detuning required, thereby alleviating an electromagnetic interference problem that might be caused by using a series inductor.

2. A cardiac pacemaker as described in claim 1, said voltage breakdown device comprising a zener diode having a sufficiently high breakdown voltage to avoid demodulation of electrosurgery signals.

3. A cardiac pacemaker as described in claim 1, said capacitor being about 0.047 microfarad.

4. A cardiac pacemaker as described in claim 2, said zener diode having about a 9.1 volt breakdown voltage.

5. A cardiac pacemaker as described in claim 1, said attaching means being provided for attaching a lead in a bipolar configuration with a tip and a ring and said protection circuit being connected across said tip and ring.

6. A cardiac pacemaker as described in claim 1, said attaching means being provided for attaching a lead in a unipolar configuration with a tip and with the housing forming the other electrode, and said protection circuit being connected across said tip and housing.

7. A cardiac pacemaker as described in claim 5, said breakdown device providing a relatively high breakdown voltage in only one direction across the tip and ring.

8. A cardiac pacemaker as described in claim 6, said breakdown device providing a relatively high breakdown voltage in only one direction across the tip and housing.

9. A cardiac pacemaker having combined defibrillation and electrosurgery protection which comprises:
   an implantable housing;
   a pacing circuit located within said housing;
   means for attaching a lead to said housing in a bipolar configuration;
   a protection circuit located between the pacing circuit and said attaching means, said protection circuit being connected across said tip and ring;
   said protection circuit comprising a zener diode and a capacitor connected across said zener diode;
   said zener diode having a sufficiently high breakdown voltage to avoid demodulation of electrosurgery signals;
   said capacitor having a value to provide a relatively low impedance with respect to electrosurgery frequencies and a relatively high impedance with respect to cardiac myopotential frequencies, said protection circuit having no series inductor whereby there is no tuned circuit nor is detuning required, thereby alleviating an electromagnetic interference problem that might be caused by using a series inductor.

10. A cardiac pacemaker having combined defibrillation and electrosurgery protection which comprises:
    an implantable housing;
    a pacing circuit located within said housing;
    means for attaching a lead to said housing in a unipolar configuration with a tip and with the housing forming the other electrode;

a protection circuit located between the pacing circuit and said attaching means, said protection circuit being connected across said tip and housing;

said protection circuit comprising a zener diode and a capacitor connected across said zener diode;

said zener diode having a sufficiently high breakdown voltage to avoid demodulation of electrosurgery signals;

said capacitor having a value to provide a relatively low impedance with respect to electrosurgery frequencies and a relatively high impedance with respect to cardiac myopotential frequencies, said protection circuit having no series inductor whereby there is no tuned circuit nor is detuning required, thereby alleviating an electromagnetic interference problem that might be caused by using a series inductor.

* * * * *